(12) United States Patent
Bodo et al.

(10) Patent No.: US 11,583,260 B2
(45) Date of Patent: Feb. 21, 2023

(54) METHOD AND DEVICE FOR PREDICTING AND TESTING PHYSIOLOGICAL CONDITIONS OF A FEMALE MAMMAL

(71) Applicant: Zajzon Bodo, Budapest (HU)

(72) Inventors: Zajzon Bodo, Budapest (HU); Akos Bodo, Godollo (HU)

(73) Assignee: Zajzon Bodo, Budapest (HU)

( * ) Notice: Subject to any disclaimer, the term of this patent is extended or adjusted under 35 U.S.C. 154(b) by 1062 days.

(21) Appl. No.: 16/313,530

(22) PCT Filed: Jun. 30, 2016

(86) PCT No.: PCT/HU2016/050030
§ 371 (c)(1),
(2) Date: Dec. 27, 2018

(87) PCT Pub. No.: WO2018/002678
PCT Pub. Date: Jan. 4, 2018

(65) Prior Publication Data
US 2019/0192122 A1   Jun. 27, 2019

(51) Int. Cl.
*A61B 5/01* (2006.01)
*A61B 10/00* (2006.01)
(Continued)

(52) U.S. Cl.
CPC ............ *A61B 10/0012* (2013.01); *A61B 5/01* (2013.01); *G01N 33/487* (2013.01);
(Continued)

(58) Field of Classification Search
None
See application file for complete search history.

(56) References Cited

U.S. PATENT DOCUMENTS

| | | | |
|---|---|---|---|
| 2010/0141772 A1* | 6/2010 | Inaguma | G01S 3/7864 348/169 |
| 2011/0190595 A1* | 8/2011 | Bennett | A61B 1/05 600/300 |

(Continued)

*Primary Examiner* — Eileen M Adams
(74) *Attorney, Agent, or Firm* — Olson & Cepuritis, Ltd.

(57) ABSTRACT

The invention relates to a method for predicting and testing physiological conditions of a female mammal related to an increased level of ferning present in a dried mucous body fluid sample of the female mammal, comprising: capturing an image of the dried mucous body fluid sample via a camera of a mobile telecommunication device through a magnifying lens releasably coupled to an objective of the camera, detecting the presence of crystals in the sample by processing the image, determining the crystal density within the sample from the detected crystals, predicting the physiological condition of the female mammal by comparing the crystal density to reference crystal density data, wherein increased crystal density is indicative of increased ferning level. The invention further relates to a mobile telecommunication device comprising: at least one processing unit, a user input interface, a display, a camera having an objective, a magnifying lens releasably coupled to the objective, at least one memory including computer program code, the at least one memory and the computer program code configured to, with the at least one processing unit, cause the device to perform at least the following: capture an image of a dried mucous body fluid sample of a female mammal via the camera through the magnifying lens, detect the presence of crystals in the sample by processing the image, determine crystal density within the sample from the detected crystals, predict a physiological condition of the female mammal related to an increased level of an ferning by comparing the crystal density to at least one reference density, wherein increased crystal density is indicative of increased ferning level.

17 Claims, 3 Drawing Sheets

(51) Int. Cl.
*G01N 33/487* (2006.01)
*G06T 7/00* (2017.01)
*G16H 50/20* (2018.01)
*G16H 50/30* (2018.01)
*G16H 40/63* (2018.01)
*G16H 40/67* (2018.01)
*G16H 30/40* (2018.01)
*G16H 30/20* (2018.01)
*G16H 10/20* (2018.01)
*G16H 10/40* (2018.01)

(52) U.S. Cl.
CPC ........... *G06T 7/0012* (2013.01); *G16H 30/20* (2018.01); *G16H 30/40* (2018.01); *G16H 40/63* (2018.01); *G16H 40/67* (2018.01); *G16H 50/20* (2018.01); *G16H 50/30* (2018.01); *A61B 2010/0019* (2013.01); *A61B 2010/0025* (2013.01); *G06T 2207/30024* (2013.01); *G16H 10/20* (2018.01); *G16H 10/40* (2018.01)

(56) References Cited

U.S. PATENT DOCUMENTS

| | | | |
|---|---|---|---|
| 2012/0044409 A1* | 2/2012 | Uchiyama | G03B 3/10 348/E5.045 |
| 2014/0313322 A1* | 10/2014 | Denise | G01N 33/487 348/135 |
| 2016/0003837 A1* | 1/2016 | Murtha | C12N 15/1138 435/6.12 |

* cited by examiner

METHOD AND DEVICE FOR PREDICTING AND TESTING PHYSIOLOGICAL CONDITIONS OF A FEMALE MAMMAL

CROSS-REFERENCE TO RELATED APPLICATION

This application is a U.S. National Stage of PCT/HU2016/050030, filed Jun. 30, 2016, which is incorporated herein by reference.

The present invention relates to a method and a mobile communication device for predicting and testing physiological conditions of a female mammal related to ferning caused by an increased level of an oestrogen hormone present in a mucous body fluid sample of the female mammal.

The invention intends to predict the time of ovulation. The invention also intends to test early pregnancy during the luteal phase. In addition, the invention intends to predict the possible date of labour and when the possible date of labour is predicted to be pre-term then the invention can help predict imminent pre-term birth. Finally, the invention intends to test fertility and gynaecology issues.

In mammals, the female ovaries produce the ova that are all present at birth. The ovulation occurs midway through the menstrual cycle in humans. About 4 days before until 1 days after ovulation is the most fertile period. Technically speaking, pregnancy is only possible during these days, which are also called the 'fertile window' in a woman's cycle, when the lifespan of the sperm (about 5 days) and the lifespan of the ovum (about 1 day) coincide and conception can occur.

Within the 'fertile window', the probability of conception rises steadily until the very day of ovulation, then the probability of conception declines rapidly by 1 day after the ovulation, thereafter a female mammal (a woman) is no longer able to get gestated (pregnant) during that menstrual cycle.

In a dried specimen of mucous body fluid sample (e.g. saliva, cervical mucus) a fern-like pattern appears due to the crystallisation of sodium chloride and potassium chloride on mucus fibres, which consists of a branched heterogeneous network. This phenomenon is called ferning, which is caused by the increased level of body oestrogen.

Georgios Papanicolaou described in 1945 how crystals were formed when a drop of cervical mucus was placed on a saline-free glass slide and allowed to air dry.

Rydberg and Madsen (Rydbergm E. and Madsen V 1948. Acta Obst. And Gynec. Scandinav. 28:386) characterized the crystals to be common salt and the formation of the crystals was shown to be due to the prescience of mucine.

Zondek and Rozin reported in 1954 (Zondek, B. and Rozin, S. 1954 Obst. and Gynec. 3: 463) that the crystallization is not specific for cervical mucus and that the same phenomenon appears in all mucus secretions and in most body fluids.

Accordingly, the chances of conceiving can be substantially increased by observing ferning and predicting the day of ovulation in advance. The oestrogen level peaks just before ovulation and so does the ferning. At about the time of ovulation, progesterone level starts to increase, and when there is no conception, progesterone hinders further ferning. The information how ferning proceeds ultimately helps to increase the probability of conception by determining the adequate time for intercourse or insemination. This issue is of utmost importance for humans, as one in six couples have difficulty with conception. However, the time of ovulation depends on the individual's cycle, which may also vary from month to month, whereby alternative solutions e.g. calendar tracking or basal body temperature measurements are not as efficient as fern test for predicting the 'fertile window'.

The fern-shaped pattern can be detected with about 100× magnification and it can be none, partial and full.

None-ferning means there is nothing to find on the slide only a few dots and maybe a few lines or crooked angular lines with air bubbles creating circles and cells appearing as spots.

Partial-ferning means the beginning of ferning when one finds lines and angular lines on the slide with some cross-hatching.

Full-ferning means there are fern-shaped patterns all over on the slide. The more ferns one can see, the higher level of oestrogen is present in the sample.

In 2014, the U.S. Food and Drug Administration (FDA) published on its website its approval of the saliva fern test as a home use test. None of the other home use tests (ovulation calendar, basal body temperature measurements) are FDA-approved because these cannot give a clinically precise prediction of the time of ovulation.

Currently available products for carrying out the saliva fern test allow users to make the visual observation themselves when ferning appears prior to ovulation. These products are, however, mere analogue mini microscopes and cannot digitalise and help analyse the presence and the density of the fern-shaped crystals.

It is an objective of the present invention to overcome the problems associated with the prior art in ovulation prediction. In particular, it is an objective of the invention to digitalise the FDA-approved, non-invasive, home-use saliva fern test for predicting the likely time of ovulation and eventually help women conceive. Additionally, the test is adapted to be conveniently carried out with a smart phone or similar mobile telecommunication device having a built-in camera that is generally available to potential users. The invention is neither limited to saliva samples nor to humans as the scope of the FDA-approved saliva fern test.

Another objective of the present invention to overcome the problems associated with the prior art in predicting the time of labour. The invention can help predict the likely time of labour because ferning is normally absent during the second half of pregnancy but it appears about 4 weeks before labour. More importantly, when the predicted time of labour is pre-term, it can be used to predict the time of pre-term birth, and eventually can help medical assistance take actions against pre-term birth.

Additional objective of the invention to overcome the problems associated with the prior art in testing early pregnancy because persisting ferning may indicate possible pregnancy even before missing menstrual period.

Other objectives of the invention are to overcome the problems associated with the prior art in testing fertility and gynaecology issues because ferning at unexpected times can also indicate fertility issues like oestrogen dominance, unovulatory cycle, PCOS or infertility.

These objectives are achieved by a method according to claim 1 and a mobile telecommunication device according to claim 17.

Advantageous embodiments of the invention are defined in the attached dependent claims.

The present invention helps collect and store sample arrays of dried mucous body fluids, e.g. saliva, cervical mucus, in a digital database for further procession, which eventually allows the automation of inter alia ovulation prediction in a standardised way.

Further details of the invention will be apparent from the accompanying figures and exemplary embodiments.

Figure 1A:
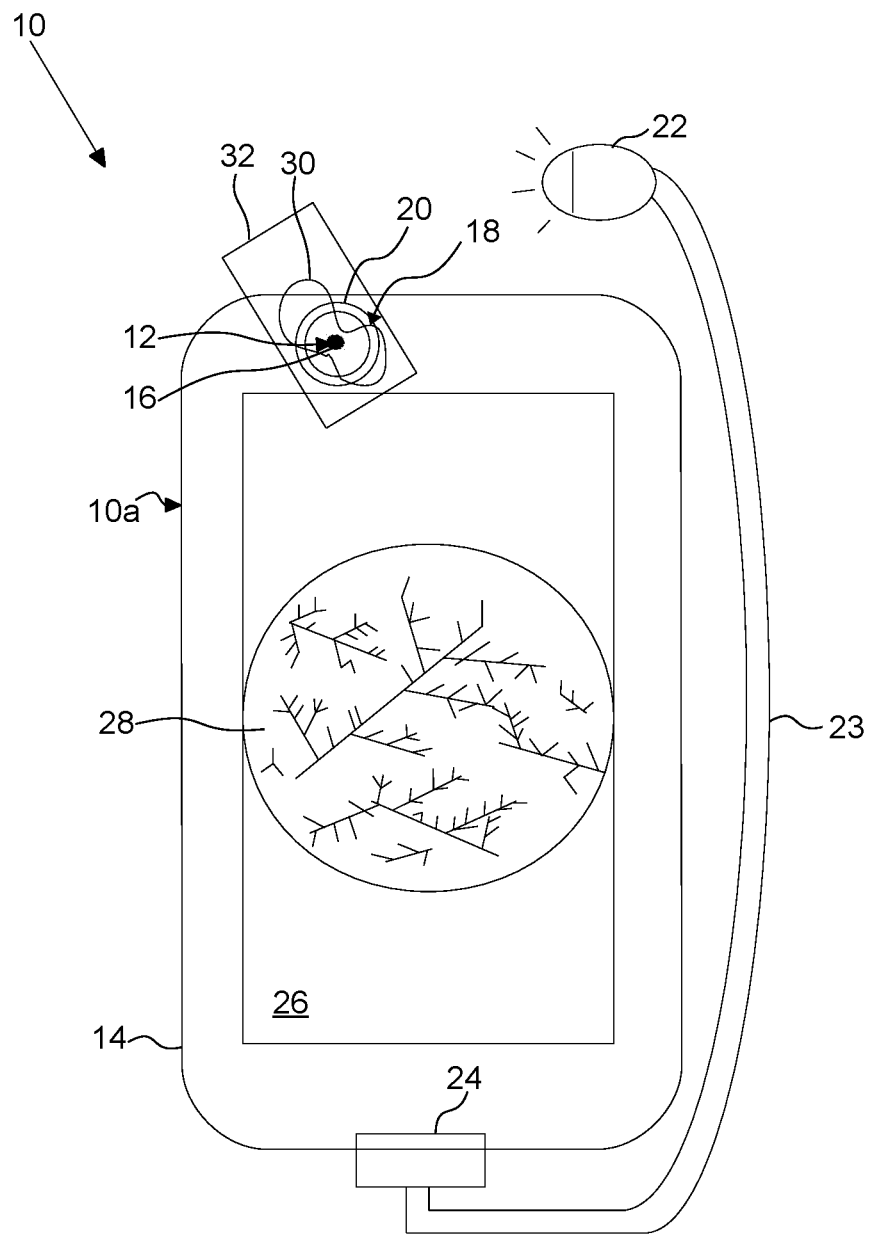
FIG. 1a is a schematic front view of an exemplary embodiment of a mobile telecommunication device according to the invention.

FIG. 1a schematically illustrates an exemplary embodiment of a mobile telecommunication device 10 in accordance with the present invention. The present embodiment is a smart phone 10a, however, other similar mobile telecommunication devices 10 may be used as well, such as a tablet 10b illustrated in FIG. 1b. Corresponding components of the smart phone 10a and the tablet 10b are indicated with the same reference numeral for the sake of simplicity.

The smart phone 10a can be any conventional smart phone equipped with a camera 12. The camera 12 is located within a housing 14 of the smart phone 10a such that a hole is formed in the housing 14 allowing light to enter an objective 16 of the camera 12. The smart phone 10a is further provided with a magnifying lens 18 that is releasably coupled to the objective 16 of the camera 12. The coupling means an optical coupling, however the lens 18 is also physically attached to the housing 14 of the smart phone 10a in any convenient way, e.g. the lens 18 may be provided with a frame 20 that has a self-adhering back side for sticking on the housing 14 and peeling off over and over. Other means may be used to attach the lens 18, e.g. the frame 20 may include a clamping mechanism for holding onto the housing 14.

The magnifying lens 18 is a lens within the range of 50× to 200× magnification, and preferably of 100× magnification.

Preferably, the smart phone 10a further comprises a light source 22 such as a LED lamp that can be coupled to an input/output port 24 of the smart phone 10a. Preferably the light source 22 is coupled to the same input/output port 24 which is used for charging the smart phone 10a. The light source 22, in particular its stem 23 is dimensioned so as to allow illumination of the lens 18 and its vicinity when it is coupled to the camera objective 16. If the smart phone 10a does not have a suitable light source 22 an external light source can be used to carry out the examination, such as a desktop lamp, or even natural light may suffice in daytime.

The smart phone 10a further includes a display 26, which is used to display an image 28 of the camera's field of view through the objective 16 and the magnifying lens 18, when a sample 30 on a transparent slide 32 is placed before the lens 18. The transparent slide 32 can be a thin glass or plastic plate. It is noted that most smart phones 10a have a front camera 12 (indicated in FIG. 1a) as well as a back camera (not shown). Either of the two cameras 16 can be used for carrying out the examination. It is more convenient to place the slide 32 on the magnifying lens 28 coupled with the front objective 16 of the front camera 12 when the camera image 28 is viewed real-time on the display 26. However, some front cameras 12 have a lower resolution than the back camera of the device 10. Preferably the resolution of the camera 12 that is used is at least 3 megapixel or preferably 5 megapixel or more.

Figure 1B:
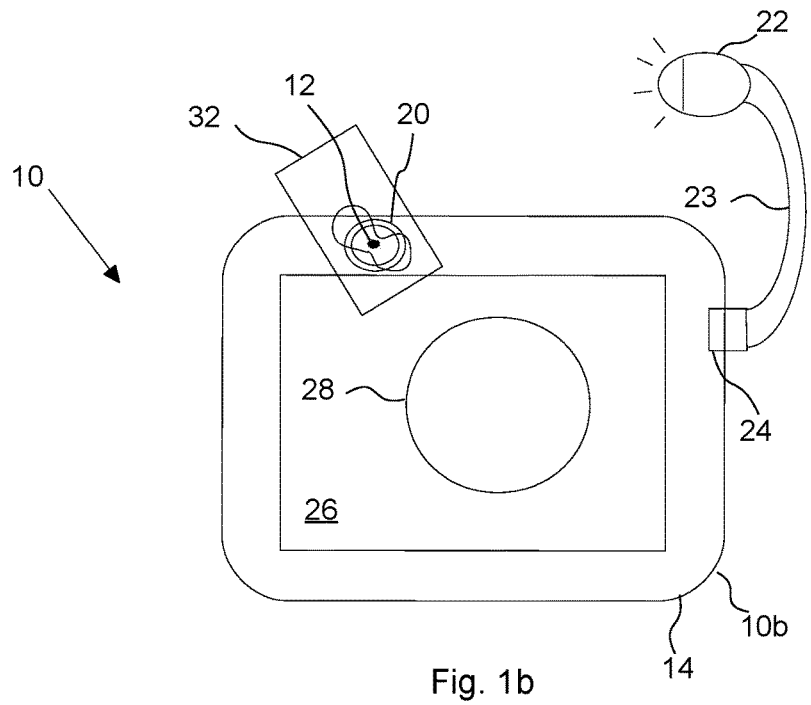
FIG. 1b is a schematic front view of another exemplary embodiment of a mobile telecommunication device according to the invention.

The tablet 10b illustrated in FIG. 1b has a similar structure as indicated by the same reference numerals and will therefore not be discussed separately.

Figure 2:
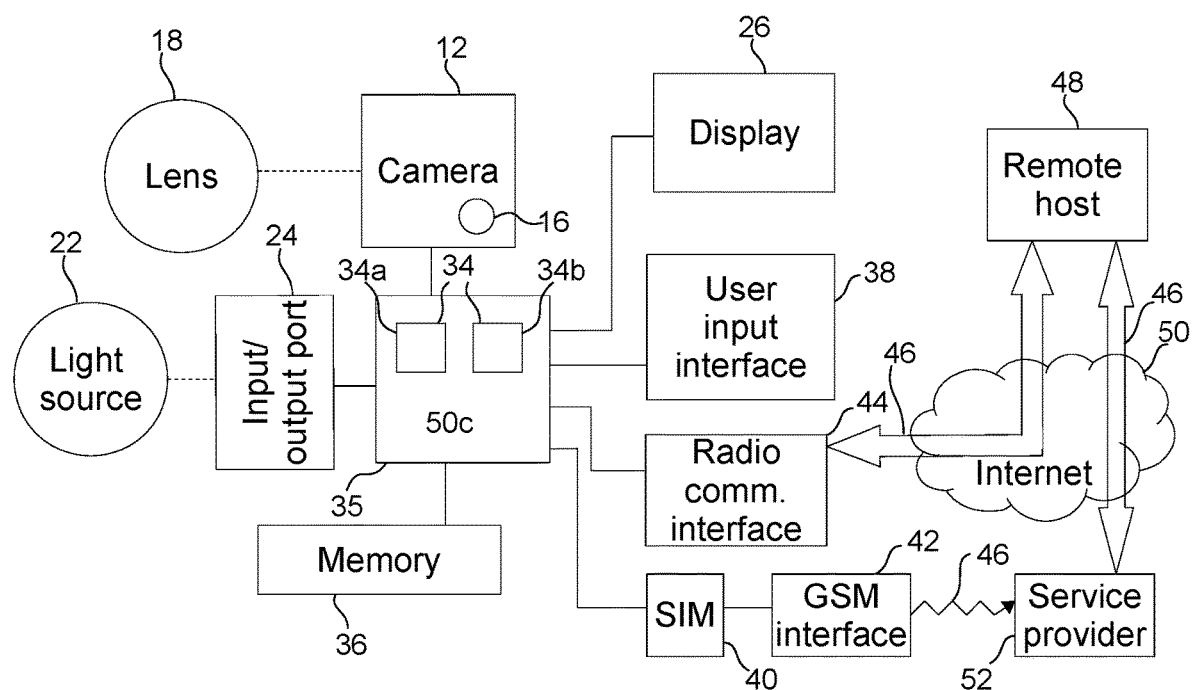
FIG. 2 is a block diagram of an exemplary embodiment of a mobile telecommunication device and cooperating infrastructure.

The main components of an exemplary mobile telecommunication device 10, which may correspond to the smart phone 10a depicted in FIG. 1a or the tablet 10b depicted in FIG. 1b, will now be discussed with reference to FIG. 2.

The device 10 comprises in addition to the components already discussed in connection with FIG. 1a at least one processing unit 34, at least one memory 36 and a user input interface 38. The processing unit may be any type of processing unit generally used in smart phones 10a, tablets 10b and similar mobile telecommunication devices. The device 10 may include more than one processing unit 34, in a preferred embodiment the device 10 comprises a central processing unit (CPU) 34a and a graphical processing unit (GPU) 34b, which are both integrated on a system on chip (SOC) 35 as illustrated in FIG. 2.

The at least one memory 36 may be any conventional non-transitional data storage type that is generally incorporated in smart phones 10a and similar devices for storing a non-transitional program. An external data storage such as a memory card or stick may be used as well.

The user input interface 38 is preferably a touch screen that is formed integrally with the display 26, however separate user input interfaces 38 may be used as well, such as a keyboard, mouse, etc.

The mobile telecommunication device 10 generally includes a SIM card 40 and a GSM interface 42 for communication over a GSM network. Any standard communication protocol may be used, e.g. 2G, 3G, 4G. Smart phones 10a, tablets 10b and similar mobile telecommunication devices 10 generally comprise one or more other radio communication interface 44 as well, such as a WIFI modem or Bluetooth modem (the latter being often incorporate in the former), which also allow for data communication over a distance, thus a SIM card is not indispensable.

In a preferred embodiment an electronic data communication channel 46 may be established between the mobile communication device 10 and a remote host 48, e.g. over the Internet 50 using the radio communication interface 44 (e.g. WIFI modem) of the device 10 or over the GSM network using the GSM interface 42 with the interposition of a mobile service provider 52 in a known way. The remote host 48 can be a server or computer, or a plurality or servers and/or computers in the "cloud" as is well known.

A computer program code is stored on the at least one memory 36, which when executed by the at least one processing unit 34 causes the mobile communication device 10 to perform at least the following:

capture the image 28 of the dried mucous body fluid sample 30 of a female mammal, in particular of a female human with the help of the camera 12 through the magnifying lens 18, detect the presence of crystals in the sample 30 by processing the image, determine crystal density within the sample 30 from the detected crystals, predict and/or test a physiological condition of the female mammal related to an increased level of an ferning by comparing the crystal density to at least one reference density, wherein increased crystal density is indicative of increased ferning level and thus of the physiological condition that is to be predicted or tested.

The method according to the invention will now be described in more detail with reference to the flow diagram of FIG. 3.

The dried mucous body fluid sample 30 of the female mammal, in particular of a woman is placed on the transparent slide 32. The transparent slide 32 is placed in the vicinity of the magnifying lens 18, preferably such as to abut the frame 20 of the magnifying lens 18. After this, in step 100, the transparent slide 32 is preferably illuminated from its opposite side via the light source 22, however, natural light may suffice during daytime. In step 102 the camera 12 captures an image of the sample 30 that is located on the slide 32 through the magnifying lens 18. The field of view of the optical system made up of the camera 12 and the magnifying lens 18 is relatively small (e.g. 2×2 mm), hence in order to facilitate detection of ferning preferably a plurality of images with slightly overlapping fields of view are captured e.g. in the form of a video recording, and the images are joined to form a larger image. This technique is well known and commonly used to obtain segmented panoramas (also called stitched panoramas). Multiple images of the same or substantially same field of view can also be used to obtain a single image of better quality for further image processing steps by combining the information content of more than one images The next step 104 comprises detecting the presence of crystals in the sample 30 by processing the image. Various suitable image processing algorithms are known in the field of computer vision, e.g. edge detection can be used to detect crystals or convolutional neural networks can be applied in a known way.

Beyond detecting the crystals the next step is to determine the crystal density on a standard slide, preferably with a 2×2 cm field, within the sample 30.

Preferably, the measured crystal density is compared to reference crystal density data, which may be stored in the memory 36 of the mobile telecommunication device 10.

The reference crystal density data preferably includes previously determined crystal densities in previously captured images of dried mucous body fluid samples of the same or other women. The reference crystal density data may be in any form, for example it may be a numerical value or a set of numerical values signifying one or more thresholds respectively for the examined physiological condition or different stages thereof respectively. The term "reference crystal density data" is understood to include the possibility that the previously captured images are stored and used for comparison with the currently captured image or combined image or plurality of images.

Based on the comparison, in step 106 a prediction is made concerning the physiological condition wherein increased crystal density is indicative of increased ferning level and thereby of the physiological condition.

Figure 3:
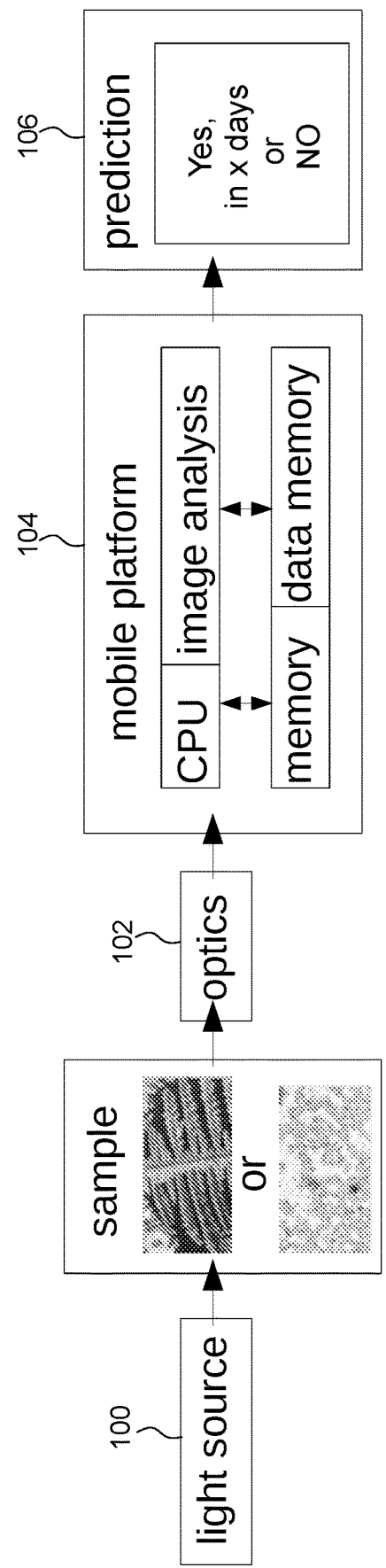
FIG. 3 is a schematic flow diagram of an exemplary method according to the invention.

In the example illustrated in FIG. 3 the examined physiological condition that is related to an increased level of an ferning is ovulation. In this case the sample 30 is a dried saliva sample. The ferning level rises before ovulation and increases up to ovulation, hence the higher the crystal density the closer the ovulation. Based on the reference crystal density data the number of days remaining until expected ovulation can be predicted, which number is zero if the measured crystal density corresponds to a crystal density signifying ovulation. Since the peak crystal density varies from female to female, it is advantageous to store the images or crystal density information of the images captured in previous menstrual cycles of the examined female and use these as reference data for determining the proximity of ovulation. If no prior data is available for the examined female, preferably averaged reference data is used, which is obtained from prior clinical tests performed on other females and/or from prior user tests performed on user devices 10. Comparison with personal reference data and averaged reference data can be combined, e.g. averaged reference data is used as a basis, however, if prior personal tests have shown that the examined female has a generally lower or higher crystal density, then the averaged reference data is corrected (decreased or increased) accordingly.

The user may provide saliva sample 30 every day or only during a shorter period (e.g. 4-6 day) in advance of a coarsely predicted ovulation day, e.g. based on personal or statistical menstrual cycle data. According to this preferred embodiment the user is prompted by the computer program code (mobile application) running on the user's mobile telecommunication device 10 (e.g. smart phone 10a or tablet 10b) to input menstrual cycle day data via the user input interface 38 (e.g. touchscreen) of the mobile telecommunication device. This can be done by prompting the user (who may or may not coincide with the examined women) to enter, as menstrual cycle day data, information about the intensity of any menses or spotting on the given day. The first day of each period is the starting day of each menstruation. The menstrual cycle data inputted by the user is compared with reference menstrual cycle day data, and the result of the comparison is used for predicting ovulation. The reference menstrual cycle day data includes previously inputted menstrual cycle day data of the same female but it may also rely on statistical menstrual cycle day data. For example statistically women have their ovulation 14 days before the end of their period, and the statistical average period is 28 days long, thus if first day of the period is known, then menstrual cycle day data corresponding to the 14th day of the menstrual cycle (of the given period) is indicative of ovulation. If personal data is available and the first day of the period is known, then the statistical 14 days can be deducted from the average period length of the examined women and the user will be prompted to provide samples 4-6 day in advance of the thus calculated day.

The inputted menstrual cycle day data may serve to calculate and provide a sampling schedule for the user, such that the user is prompted to provide saliva samples 30 within a couple of days (e.g. 4-6 days) prior to the day of ovulation coarsely determined from the inputted menstrual cycle day data.

It is further advantageous to combine the above described saliva fern test with conventional basal body temperature measurement. The computer program code (mobile application) running on the user's mobile telecommunication device 10 (e.g. smart phone 10a or tablet 10b) preferably prompts the user to input temperature data via the user input interface 38 (e.g. touchscreen) of the device 10. The user can be prompted to do so every day or only within a shorter period in advance of the coarsely predicted ovulation day as explained above. It is particularly advantageous to compare the temperature data with reference (personal or statistical) temperature data, and use the result of the comparison for predicting ovulation in combination with the saliva fern test, such that an increased temperature is indicative of ovulation. Preferably the reference temperature data includes previously inputted temperature data of the same female. In a preferred embodiment the sampling schedule for the saliva fern test is provided on the basis of the inputted temperature data. When a rise in the basal temperature is detected, which is indicative of an upcoming ovulation, the user is prompted to provide a saliva sample 30 for carrying out the saliva fern test.

The above described steps 100, 102, 104 and 106 may all be carried out by the mobile telecommunication device 10, in particular the at least one memory 36 and the computer program code stored therein may be configured to, with the at least one processing unit 34, cause the device 10 to perform the above described steps. However, it is also possible to carry out some of the method steps by the remote host 48. This has the advantage that a larger database and higher calculation capacity may be available at the remote host 48 whereby more complex comparison and prediction can be performed if steps 104 and 106 are carried out by the remote host. According to a preferred embodiment the data relating to the determined crystal density is electronically transmitted from the mobile telecommunication device 10 to a remote host. The data is transmitted with the help of the radio communication interface 44 or the GSM interface 42 of the device 10 depending on the network (e.g. Internet 50, GSM network 46) to be used.

The physiological condition of the female can then be predicted at the remote host 48. A substantially larger database may be available at the remote host 48 than what can be stored on a smart phone 10a or tablet 10b or similar device 10. The calculation capacity can also be far greater at the remote host 48, especially if it is a server or a plurality of computers working in a grid or similar system. It is also possible to send the raw data (one or more image files) and perform the crystal detection and crystal density determination at the remote host 48 as well, however, the transmission of larger files may be disadvantages if the mobile telecommunication device 10 does not have access to Internet and only the GSM network can be used.

Once the prediction of the examined physiological condition has been performed at the remote host 48 the data relating to the result of the prediction is transmitted back from the remote host 48 to the mobile telecommunication device 10 using the available electronic communication network (e.g. Internet 50 or GSM network 46).

The result of the prediction is displayed on the display 26 of the mobile telecommunication device 10.

In a preferred embodiment the captured images or a single image obtained from the captured images is saved on either the mobile telecommunication device 10 (in its memory 36) or at the remote host 48 for future viewing.

The inventors have realised that the above described method can be applied for the prediction of physiological conditions other than ovulation, which are related to an increased level of ferning present in a dried mucous body fluid sample of a female mammal. Such other physiological condition is early pregnancy, which is also accompanied by an increased ferning level. When the method according to the invention is used for testing early pregnancy it has been found that, it is possible to detect crystals in the dried cervix mucus sample and also in the dried saliva sample of female mammals at an early stage of pregnancy. When performing early pregnancy prediction from a cervix mucus sample the user is preferably a gynaecologist or a veterinary, however medically non-qualified persons such as the women wishing to know her condition or a breeder wishing to know the condition of her female mammal can easily learn to take cervix mucus sample without the aid of a gynaecologist or a veterinary, respectively.

Another physiological condition that may be predicted with the method according to the invention is a condition associated with the prediction of the time of labour (after 24 week pregnancy), which can also be applied to predict an the likely time of labour and when the predicted time of labour is pre-term the physiological condition is the increased risk of preterm birth. It has been found that birth is preceded by full ferning from samples taken from a mucous body fluid sample, whereby the inventors have found that an increased risk of preterm birth can also be detected by the method and device 10 according to the invention. The sample is preferably a dried cervix mucus sample although increased ferning level can also be detected in a dried saliva sample. The method is preferably performed by a gynaecologist or a veterinary, however, other persons may carry out the test as well, including the possibility of self-examination.

Other physiological conditions that may be tested with the method according to the invention is a condition associated with testing fertility and gynaecology issues because ferning at unexpected times can also indicate fertility issues like oestrogen dominance, unovulatory cycle, PCOS or infertility.

One of the advantages of the present invention is that it does not require any additional hardware apart from the magnifying lens 18, since potential users generally possess at least a smart phone 10a. The computer program code is preferably a mobile application that can be simply downloaded and installed on a smart phone 10a, tablet 10b or similar device 10. It is further advantageous to use the remote host 48 for performing steps requiring greater calculation capacity, whereby the mobile telecommunication device 10 need not have a particularly strong hardware configuration. It is a further advantage that a large database can be used for storing reference crystal density data (including the possibility of storing reference image files), whereby a much more accurate prediction is possible than on the mobile platform of the device 10.

Various modifications to the above disclosed embodiments will be apparent to a person skilled in the art without departing from the scope of protection determined by the attached claims.

The invention claimed is:

1. A method for predicting and/or testing a physiological condition of a female mammal related to ferning caused by an increased level of an oestrogen hormone present in a mucous body fluid sample of the female mammal using a hand-held mobile telecommunication device, comprising:
   capturing an image of the dried mucous body fluid sample via a camera of a mobile telecommunication device selected from a group consisting of a smart phone and a tablet through a magnifying lens releasably coupled to an objective of the camera,
   detecting the presence of crystals in the sample by processing the image using the hand-held mobile telecommunication device,
   determining the crystal density within the sample from the detected crystals using the hand-held mobile telecommunication device, and
   predicting and/or testing the physiological condition of the female mammal by comparing the crystal density to reference crystal density data, wherein increased crystal density is indicative of increased ferning level.

2. The method according to claim 1, wherein the magnifying lens is a lens with a range of 50× to 200× magnification.

3. The method according to claim 1, wherein the reference crystal density data includes previously determined crystal densities in previously captured images of dried mucous body fluid samples of the same or other female mammals.

4. The method according to claim 1, wherein the sample is a dried saliva sample and the physiological condition is ovulation.

5. The method according to claim 1, wherein the sample is a dried saliva or cervix mucus sample and the physiological condition is early pregnancy.

6. The method according to claim 1, wherein the sample is a dried saliva or cervix mucus sample and the physiological condition is the likely time of labour and when the predicted time of labour is pre-term the physiological condition is the increased risk of preterm birth.

7. The method according to claim 1, wherein the sample is a dried saliva or cervix mucus sample and the physiological condition is fertility disorder caused by at least one of oestrogen dominance, unovulatory cycle, PCOS, infertility.

8. A method for predicting and/or testing a physiological condition of a female mammal related to ferning caused by an increased level of an oestrogen hormone present in a mucous body fluid sample of the female mammal, comprising:
    capturing an image of the dried mucous body fluid sample via a camera of a hand-held mobile telecommunication device selected from a group consisting of a smart phone and a tablet through a magnifying lens releasably coupled to an objective of the camera,
    detecting the presence of crystals in the sample by
    capturing a plurality of dried mucous body fluid sample images in the form of a video recording using the hand-held mobile telecommunication device,
    determining the crystal density within the sample from the detected crystals using the hand-held mobile telecommunication device, and
    predicting and/or testing the physiological condition of the female mammal by comparing the crystal density to reference crystal density data, wherein increased crystal density is indicative of increased ferning level.

9. A method for predicting and/or testing a physiological condition of a female mammal related to ferning caused by an increased level of an oestrogen hormone present in a mucous body fluid sample of the female mammal, comprising:
    capturing an image of the dried mucous body fluid sample via a camera of a mobile telecommunication device selected from a group consisting of a smart phone and a tablet through a magnifying lens releasably coupled to an objective of the camera,
    detecting the presence of crystals in the sample by processing the image,
    determining the crystal density within the sample from the detected crystals,
    electronically transmitting data relating to the determined crystal density from the mobile telecommunication device to a remote host,
    predicting the physiological condition of the female mammal at the remote host by comparing the crystal density to reference crystal density data, wherein increased crystal density is indicative of increased ferning level,
    transmitting back data relating to the result of the prediction from the remote host to the mobile telecommunication device, and
    displaying the result of the prediction on a display of the mobile telecommunication device.

10. A hand-held mobile telecommunication device selected from a group consisting of a smart phone and a tablet and comprising:
    at least one processing unit,
    a user input interface,
    a display,
    a camera having an objective,
    a magnifying lens releasably coupled to the objective,
    at least one memory including computer program code in the hand-held mobile telecommunication device, the at least one memory and the computer program code configured to, with the at least one processing unit, cause the hand-held device to perform at least the following:
    capture an image of a dried mucous body fluid sample of a female mammal via the camera through the magnifying lens,
    detect the presence of crystals in the sample by processing the image,
    determine crystal density within the sample from the detected crystals,
    predict and/or test a physiological condition of the female mammal related to an increased level of ferning by comparing the crystal density to at least one reference density, wherein increased crystal density is indicative of increased ferning level.

11. The mobile telecommunication device according to claim 10, wherein the magnifying lens is a lens with the range of 50× to 200× magnification.

12. The mobile telecommunication device according to claim 10, wherein the reference crystal density data includes previously determined crystal densities in previously captured images of dried mucous body fluid samples of the same or other female mammals.

13. The mobile telecommunication device according to claim 10, wherein the sample is a dried saliva sample.

14. The mobile telecommunication device according to claim 10, wherein the sample is a dried saliva or cervix mucus sample and the physiological condition is early pregnancy.

15. The mobile telecommunication device according to claim 10, wherein the sample is a dried saliva or cervix mucus sample and the physiological condition is the likely time of labour and when the predicted time of labour is pre-term the physiological condition is the increased risk of preterm birth.

16. The mobile telecommunication device according to claim 10, wherein the sample is a dried saliva or cervix mucus sample and the physiological condition is fertility disorder caused by at least one of oestrogen dominance, unovulatory cycle, PCOS, infertility.

17. The mobile telecommunication device according to claim 10, wherein the mobile telecommunication device comprises a light source that can be coupled to an input/output port of the mobile telecommunication device.

* * * * *